United States Patent [19]

Pohl et al.

[11] Patent Number: 5,220,047

[45] Date of Patent: Jun. 15, 1993

[54] CARBAMATE SILICON COMPOUNDS AS LATENT COUPLING AGENTS AND PROCESS FOR PREPARATION AND USE

[75] Inventors: Eric R. Pohl, Tarrytown; Curtis L. Schilling, Jr., Croton-On-Hudson, both of N.Y.

[73] Assignee: Union Carbide Chemicals & Plastics Technology Corporation, Danbury, Conn.

[21] Appl. No.: 582,082

[22] Filed: Sep. 17, 1990

[51] Int. Cl.$^5$ ............................................. C07F 7/02
[52] U.S. Cl. ............................................. 556/420
[58] Field of Search ............................................. 536/420

[56] References Cited

U.S. PATENT DOCUMENTS

| | | | |
|---|---|---|---|
| 3,170,891 | 2/1965 | Spier | 260/37 |
| 3,494,951 | 2/1970 | Berger | 260/448.2 |
| 3,598,852 | 8/1971 | Berger | 260/448.2 E |
| 3,607,901 | 9/1971 | Berger | 260/448.2 N |
| 3,821,218 | 6/1974 | Berger | 260/248 NS |
| 4,631,346 | 12/1986 | Webb et al. | 556/420 |
| 4,837,349 | 6/1989 | Ohfune et al. | 556/420 |
| 4,861,908 | 8/1989 | Satoh et al. | 556/420 |
| 4,889,768 | 12/1989 | Yokoshima et al. | 556/420 X |

FOREIGN PATENT DOCUMENTS

WO9107087 11/1990 PCT Int'l Appl. .

OTHER PUBLICATIONS

Chem Abstr. 115(26), 1991, 275262a, line 27.
Mironov et al, Zhurnal Obshchei Khimii, vol. 39, No. 4, pp. 813–816, Apr., 1969.
Mironov et al, Doklady Akademii SSSR, vol. 178, No. 2, pp. 358–361, Jan., 1968.
Chem. Abstracts, vol. 87, 153208v, 1977.
Chem. Abstracts, vol. 87, 153157c, 1977.

*Primary Examiner*—Arthur C. Prescott
*Attorney, Agent, or Firm*—B. L. Deppenbrock

[57] ABSTRACT

Novel tert-alkyl carbamate silicon compounds are provided which are useful as coupling agents. The compounds have the formulas:

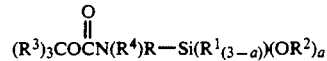

or

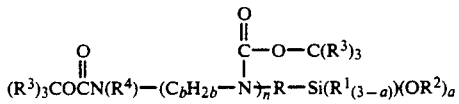

wherein the R groups can represent various hydrocarbon and other groups, n has a value of 1 to 10, b has a valueof from 2 to 5 and a has a value of 1, 2 or 3.

Processes are also provided for the preparation of the carbamate compounds and their use as coupling agents.

41 Claims, No Drawings

CARBAMATE SILICON COMPOUNDS AS LATENT COUPLING AGENTS AND PROCESS FOR PREPARATION AND USE

BACKGROUND OF THE INVENTION

1) Field of the Invention

This invention relates in general to novel silicon compounds. In one aspect, this invention is directed to tert-alkyl carbamate silicon compounds which when activated (i.e., deblocked) are particularly useful as coupling agents. In another aspect this invention is directed to tert-alkyl carbamate silicon compounds which are latent coupling agents and wherein the carbamate silicon compounds are compatible and stable in the presence of a variety of sizing and coating agents, such as antistats, lubricants, film formers and other chemicals employed in the protection of surfaces, particularly inorganic oxide surfaces, from abrasion and corrosion. The invention is also directed to processes for the preparation of novel silicon compounds, to processes for activation (deblocking) to aminosilane coupling agents, and to processes for their use in aqueous sizes for improving adhesion between resinous systems and inorganic oxide materials, particularly fiber glass.

2) Description of the Related Art

Organofunctional silane compounds have been employed in the treatment of a variety of surfaces, such as metal oxides, silicates, particulate siliceous fillers and pigments, and fibers such as glass fibers, steel fibers and aluminum fibers. (Metal surfaces are regarded as oxide surfaces because they are oxidized even though their subsurfaces are not). Some organofunctional silane treatments involve coating such a surface with an aqueous solution of the silicon compound either alone or in conjunction with other chemicals.

Other modes of treatment involve coating such surfaces with an organic or aqueous organic solution of the silicon compound either alone or in conjunction with other chemicals, or coating the surface with the silicon compound without the aid of a solvent. In some instances, the silicon compound can be added directly to the resinous media (integral blend).

As a rule, the treatment enhances bonding between the inorganic oxide surfaces and resinous media. Consequently, the silicon compounds have utility as components in primers in the application of coatings, adhesives or sealants to inorganic oxide surfaces and as a filler pretreatment to improve the strength and structural integrity of filled resin composites such as those incorporating fiber glass. Such organofunctional hydrolyzable silanes are termed "Coupling Agents" or "Adhesion Promoters".

In addition to the improvement of bonding, coupling agents have found other uses related to their ability to alter the surface characteristics of inorganic oxides, such as their ability to protect glass fibers from abrasion and impart lubricity to the glass which is important in handling and processing the glass fibers.

Prior to the present invention, it was known that 3-aminopropyltriethoxysilane and other aminosilanes were often used to treat glass fibers either as continuous strands or as woven cloth. However, a problem has been in existence for some time which detracts from the use of such silanes in the treatment of glass fibers. It has been noted that silane treated glass fibers age prematurely. The amine groups react with carbon dioxide of the air to form carbamic acids. These acids make the glass fibers stiff and difficult to handle especially in the woven form. In addition, oxygen in the air can slowly oxidize the amino functional group of the silane. The oxidation products of the amino functional group are often not reactive with the organic resins and the silane coupling agent loses its coupling efficiency. In many instances, fabrics and continuous strands comprised of fiber glass become discolored because of the oxidation of the amino functional silane and accordingly are of less value.

It has also been noted that aminosilane compounds when used as coupling agents are not always compatible with the other components in the coating, primer or size, such as size or coating materials used in the processing of glass fibers. As hereinafter indicated, glass fibers, for example, usually require the presence of other ingredients such as film formers, lubricants, antistats, and the like, in order to impart desirable characteristics to the glass fibers. The presence of aminoorganosilanes in formulations containing such ingredients may not provide a system which is stable for any length of time, especially if the other ingredients are pH sensitive emulsions, and/or contain functional groups that can react with amines, such as epoxies, carboxylates and the like. Accordingly, there is a need in such cases for aminosilanes which can remain latent when in contact with other sizing (processing) components prior to the application of these materials to the surface but can be activated when desired to serve their function as coupling agents.

Accordingly, one or more of the following objects will be achieved by the practice of the present invention. It is an object of this invention to provide certain novel silicon compounds which can be activated to function as coupling agents. Another object of the invention is to provide novel tertiary-alkyl carbamate silicon compounds which when deblocked are useful as aminosilane coupling agents. A futher object is to provide tert-alkyl carbamate silicon compounds which upon heating or in the presence of a catalyst, decompose to form unsaturated hydrocarbons, carbon dioxide and aminosilanes. Another object of this invention is to provide tert-alkyl carbamate silicon compounds in which the organofunctional groups are dormant and unreactive in the presence of a variety of additives and chemicals employed in priming of inorganic surfaces, sizing or finishing fibers, coatings of inorganic oxide surfaces or when compounded with resinous materials. Another object is to provide latent silicon compounds which do not affect the stability of systems containing sizing and/or coating agents, such as antistats, emulsifiers, and the like, but when activated, function as coupling agents. Another object is to provide processes for the preparation of the tert-alkyl carbamate silicon compounds. An object is to prepare the novel carbamates by the reaction of a tertiary alcohol and an isocyanatofunctional silane. Another object is to prepare the carbamates by the reaction of a tertiary alcohol with an alkenyl isocyanate followed by hydrosilation with an hydridosilane. A further object is to prepare novel carbamates by the reaction of a tert-alkyl phenyl carbonate or a di-tert-alkyl carbonate with an amino functional silane. Another object is to provide stable coatings for glass fibers which contain a latent silicon coupling agent, antistats, film formers, lubricants and the like. A still further object is to provide processes for activating the tert-alkyl silicon compound for the purpose of coupling resinous systems and inorganic oxide surfaces, silicates and the like. These and other objects will readily become apparent to those skilled in the art in the light of the teachings herein set forth.

SUMMARY OF THE INVENTION

In its broad aspect, this invention is directed to tertiary-alkyl carbamate silicon compounds, processes for their preparation and their uses as latent amine coupling agents in the preparation of stable coating compositions containing sizing components which might otherwise be reactive with an amine coupling agent.

DESCRIPTION OF THE PREFERRED EMBODIMENTS

The tert-alkyl carbamate silicon compounds are characterized by the unit structure:

  (I)

and wherein the remainder of the molecule contains at least one silicon atom and from 1 to 90 carbon atoms and wherein the unit structure is attached to the silicon atom through a carbon linkage. The tert-alkyl carbamate silicon compounds can also contain one or more of nitrogen, oxygen, halogen and the like, and can include silicon compounds of the formulas:

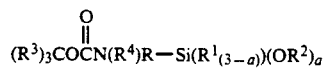  (II)

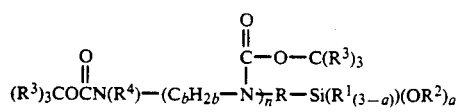  (III)

wherein:
R contains 1 to 20 carbon atoms and preferably 2 to 12 carbon atoms, and represents an arylene group, an alkarylene group, an unsaturated group or a branched or straight chain saturated group of the structure:

  (IV)

wherein x, y, and z have a value of from 0 to 20 and wherein the sum of x, y, and z is at least 1, but not greater than 20 and preferably 2 to 12, and wherein $R^5$ is an alkyl group of 1 to 6 carbon atoms, preferably 1;

$R^1$ contains 1 to 10 carbon atoms, more preferably 1 to 7 carbon atoms, and represents a straight or branched chain alkyl group, an aryl group, or an alkaryl group;

$R^2$ is the same as $R^1$ and may additionally represent hydrogen, acyl, alkoxyalkyl, such as, $CH_3OCH_2CH_2$—, or $CH_3OCH(CH_3)CH_2$—, oximato, such as $N=C(R^1)_2$ and silyl groups, including the hydrolytic condensation products thereof; $R^3$ contains 1 to 10 carbon atoms, preferably 1 to 6 carbon atoms and represents a saturated or unsaturated aliphatic group or an aryl group with the proviso that the $R^3$ groups need not be the same and the formula (I) must contain at least one $R^3$ alkyl group that contains an alpha-carbon with at least one hydrogen;

$R^4$ represents hydrogen, aryl, or a straight or branched chain alkyl group of 1 to 10 carbon atoms, or

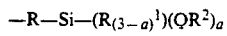

wherein
R, $R^1$ and $R^2$ are as previously indicated,
n has a value of from 1 to 10, preferably 1 to 5,
b has a value of from 2 to 5, preferably 2 and
a has a value of 1, 2 or 3.

A unique feature of the tert-alkyl carbamate silicon compounds of the present invention is their ability to be incorporated into formulations containing additives with which amine coupling agents might otherwise be reactive and thereby provide stable systems containing a latent coupling agent which can be deblocked or activated when desired.

Aminoorganosilicon compounds, such as 3-aminopropyltriethoxysilane, are unique in their ability to couple certain organic resins to glass fibers, metal oxides, siliceous fillers and other inorganic compounds. Glass fiber sizes, however, require other ingredients, such as film formers, antistats, lubricants, and the like, that may be destabilized by or react with aminoorganosilicon compounds. For example, a resin may be modified with carboxylate groups to make it water dispersible. The aminoorganosilicon compounds can form salts with these carboxylate groups and render them unable to disperse the resin. In addition, certain reactive functional groups, such as epoxides, isocyanates and the like, may be present in the size formulation. The aminoorganosilicon compounds would react with these groups.

Accordingly, the tert-alkyl carbamate organosilicon compounds of this invention make it possible to formulate complex size or coating formulations in the presence of compounds containing certain reactive functional groups by using "a latent coupling agent" which can be deblocked or activated when desired and therefore avoid undesirable side reactions of the coating ingredients with amines. A size or coating formulation containing the latent coupling agent can then be applied to glass fiber or other substrate from solution. During the drying process, in a separate heating step, or during composite fabrication, the tert-alkyl blocking (protecting) group can be removed thermally or the tert-alkyl protecting group can be removed under mild conditions by the addition of a catalyst.

As indicated above, the present invention provides novel tert-alkyl carbamate silicon compounds which are useful as latent aminosilane coupling agents. Illustrative of the silicon compounds of the present invention are the following:

Tert-butyl N-(3-trimethoxysilylpropyl)carbamate,
Tert-butyl N-(3-methyldimethoxysilylpropyl)carbamate,
Tert-butyl N-(3-dimethylmethoxysilylpropyl)carbamate,
Tert-butyl N-(4-trimethoxysilylbutyl)carbamate,
Tert-butyl N-(4-trimethoxysilylphenyl)carbamate,
Tert-butyl N-(4-trimethoxysilylbenzyl)carbamate,
Tert-butyl N-(3-triethoxysilylpropyl)carbamate,
Tert-butyl N-methyl-N-(3-trimethoxysilylpropyl)carbamate,
Tert-butyl N-phenyl-N-(3-trimethoxysilylpropyl)carbamate,
Tert-butyl N-(11-trimethoxysilylundecyl)carbamate, Tert-butyl N, N-bis-(3-trimethoxysilylpropyl) carbamate,
Tert-butyl N, N-bis-(4-trimethoxysilylbutyl) carbamate,
Tert-butyl N-(3-trimethoxysilyl-2-methylpropyl)carbamate,
Tert-butyl N-[4-(2-trimethoxysilyl)ethyl]benzyl carbamate,
Tert-pentenyl N-(3-trimethoxysilylpropyl)carbamate,
Tert-pentyl N-(3-trimethoxysilylpropyl)carbamate,
and compounds of the structures:

(MeO)$_3$Si(CH$_2$)$_3$N(boc)(CH$_2$)$_2$NH(boc),
(MeO)$_3$Si(CH$_2$)$_3$N(boc)(CH$_2$)$_2$N(boc)(CH$_2$)$_3$Si(OMe)$_3$,
(MeO)$_3$Si(CH$_2$)$_3$N(boc)(CH$_2$)$_2$N(boc)(CH$_2$)$_2$N-(boc)(CH$_2$)$_3$Si(OMe)$_3$, wherein (boc) represents the group CO$_2$C(CH$_3$)$_3$. Several synthetic routes have been used to prepare the compounds of the present invention. The synthetic routes are (a) the addition of tert-alkyl alcohols to isocyanatofunctional silanes, (b) addition of tert-alkyl alcohols to alkenyl isocyanates and then hydrosilation of the resulting carbamates with hydridosilanes, (c) the reaction of tert-alkyl phenyl (or chloro or oxime or other) carbonate with aminosilanes and (d) the reaction of tert-alkyl dicarbonates with amino functional silanes.

One synthetic route employed is illustrated in Example 1 and involves the reaction of tert-butyl alcohol with 3-isocyanatopropyltrimethoxysilane. Although the reaction proceeded slowly and with some transesterification of the silane ester, the tert-butyl N-(3-trimethoxysilylpropyl) carbamate was isolated in good yield. The reaction was found to proceed more rapidly when the starting isocyanatosilane contained a tertiary amine catalyst.

As indicated above, in this method the carbamate compounds can be synthesized by reacting a tertiary alcohol with an isocyanatosilane as illustrated below:

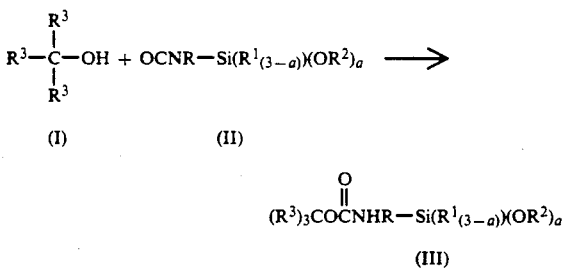

wherein R-R$^3$ and a are as previously indicated.

This reaction is conveniently conducted with or without an inert solvent, optionally in the presence of a catalyst, and at a temperature of from about 0° C. to about 120° C., more preferably from about 20° C. to about 85° C., and in a mole ratio of alcohol to isocyanate of from about 1 to about 3, and more preferably from about 1 to about 1.5.

Illustrative tertiary alcohol starting materials include, but are not limited to, alcohols such as tertiary butanol, tertiary pentanol, tertiary heptanol, diethyl phenyl carbinol, ethyl diphenyl carbinol, propyl diphenyl carbinol, dipropyl phenyl carbinol, vinyl dimethyl carbinol, and the like.

Illustrative isocyanatosilanes include among others, 3-isocyanatopropyltrimethoxysilane, 4-isocyanatobutyltrimethoxysilane, 5-isocyanatopentyltrimethoxysilane, 6-isocyanatohexyltrimethoxysilane, p-isocyanatophenyltrimethoxysilane, m-isocyanatophenyltrimethoxysilane, p-isocyanatobenzyltrimethoxysilane, 3-isocyanatopropylmethyldimethoxysilane, 3-isocyanatopropyldimethylmethoxysilane, and the like.

As indicated above, the reaction may be conducted in an inert organic solvent. Illustrative solvents are those which are unreactive with the isocyanate group and include hydrocarbons, chlorinated hydrocarbons, such as carbon tetrachloride, linear and cyclic ethers, and the like.

If desired, in some instances the reaction can be promoted by the presence of a catalyst. Suitable catalysts include, if used, among others, tertiary amines, tin compounds and compounds known to catalyze urethane formation.

In another method tert-butyl N-(2-propenyl) carbamate was reacted with trimethoxysilane in the presence of a platinum catalyst as shown in Example 2. The structure of tert-butyl N-(2-propenyl) carbamate had been previously reported by R. G. Shea in J. Org. Chem. 51, 5243-5252 (1986). V. F. Mironov et al., in Akad. Nauk SSSR 178(2), 358-61 (1968) reported the platinum catalyzed hydrosilation of ethyl N-alkenyl carbamates with hydrosilanes. The hydrosilation of sterically bulky tert-butyl N-(2-propenyl) carbamate with silanes had not been reported. This approach has the advantage that it does not cause transesterification of the silane ester with tert-butyl alcohol.

In this method the tert-alkyl carbamate silicon compounds can be prepared by reacting a tert-saturated or unsaturated N-(2-alkenyl) carbamate with a hydridosilane in the presence of a noble metal catalyst, preferably a platinum catalyst, as shown below:

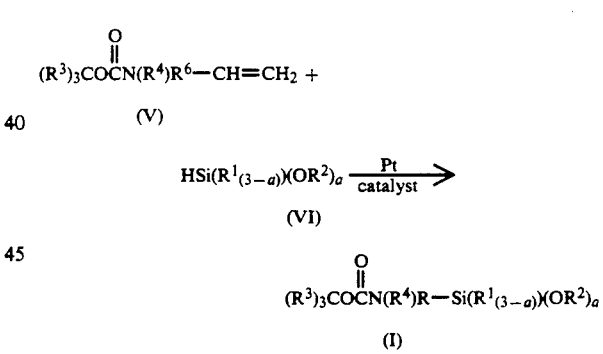

wherein R is as previously defined except that it contains from 3 to 20 carbon atoms, R$^1$-R$^4$ and a are as previously defined, and R$^6$ contains 1 to 18 carbon atoms and preferably 1 to 10 carbon atoms, and represents an arylene group, and alkarylene group, an unsaturated group or a branched or straight chain saturated group.

The carbamate (V) is conveniently prepared by the addition of a tert-alkyl alcohol to an alkenyl isocyanate or by the reaction of an alkenylamine with a chloroformate or an alkyl dicarbonate, or the like. Tert-alkyl dicarbonates, tert-alkylaryl carbonates or other compounds can be used to prepare the carbamates.

This reaction is conveniently conducted with or without an inert solvent, optionally in the presence of a catalyst, and at a temperature of from about 0° C. to about 120° C., more preferably from about 20° C. to about 85° C., and in a mole ratio of alcohol to isocyanate of from about 1 to about 3, and more preferably from about 1 to about 1.5.

Illustrative tertiary alcohol starting materials include, but are not limited to, alcohols such as tertiary butanol, tertiary pentanol, tertiary heptanol, diethyl phenyl carbinol, ethyl diphenyl carbinol, propyl diphenyl carbinol, dipropyl phenyl carbinol, vinyl dimethyl carbinol and the like.

Illustrative isocyanato alkenes include among others, allyl isocyanate, methallyl isocyanate, butenyl isocyanate, pentenyl isocyanate, heptenyl isocyanate, and the like.

Illustrative alkenylamines include allylamine, methallylamine, N-methylallylamine, N-phenylallylamine, N-methylmethallylamine, 3-butenylamine, 4-pentenylamine, 10-undecenylamine, diallylamine, dimethallylamine, 4-vinylbenzylamine, N-methyl-4-vinylbenzylamine, N-allylethylenediamine, N-allyldiethylenetriamine, N,N'-diallylethylenediamine, and the like.

The novel tert-alkyl carbamate silicon compounds can also be prepared by the reaction of aminosilanes with a di-(tert-alkyl) dicarbonate such as di(tert-butyl) dicarbonate. Illustrative amino functional silanes include the following:

3-trimethoxysilylpropylamine,
3-triethoxysilylpropylamine,
3-(dimethylmethoxysilyl)propylamine,
3-(dimethoxymethylsilyl)propylamine,
3-trimethoxysilyl-2-methylpropylamine,
N-methyl-3-trimethoxysilylpropylamine,
N-phenyl-3-trimethoxysilylpropylamine,
N-(3-trimethoxysilylpropyl)ethylenediamine,
N-(3-trimethoxysilylpropyl)diethylenetriamine,
Bis-(3-trimethoxysilylpropyl)amine,
N,N'-Bis-(3-trimethoxysilylpropyl)ethylenediamine and the like.

This reaction between aminosilanes and di-(tert-alkyl) dicarbonates can be illustrated as follows:

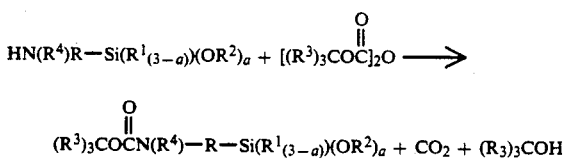

As hereinbefore indicated, the novel tert-alkyl carbamate silicon compounds have utility as latent coupling agents in coatings (sizes) for fiberglass and other applications. They are (blocked) aminosilanes, hereinafter also referred to as "dormant" or "latent" aminosilanes. They are unique in that they can be added to formulation containing emulsions, dispersions or solutions of materials (polymers) that would normally be destabilzed by alkaline pH or amine containing molecules. On heating and/or in the presence of catalysts, the tert-alkyl carbamate silicon compounds decompose to form an unsaturated hydrocarbon, carbon dioxide and aminosilanes, and can illustrated as follows:

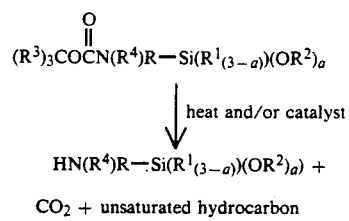

The aminosilanes are then available to couple the glass fibers or other inorganic substrate to the polymer matrix in composites or improve adhesion between organic coating materials and inorganic surfaces.

Less hindered, i.e., primary-alkyl carbamate compounds are known to decompose to primary alcohol and isocyanatosilicon compounds.

In addition to fiber glass, the inorganic oxide which can be benefically treated by the tert-alkyl carbamate silicon compounds of this invention is any inorganic solid material which possesses either oxide or hydroxyl at its exposed surface, and includes any material which can be treated by coupling agents known in the prior art. The inorganic oxide material can be in any form, including particles or irregular or regular (e.g. spherical) shape, individual fibers, woven fiber mats or fabric, or continuous surfaces such as sheets, films, slabs, and formed shapes.

Specific illustrations of suitably employed inorganic oxide materials are, for example, brass (with oxidized surface), copper metal (oxidized at its surface), iron, steel (oxidized at its surface), alumina, aluminum trihydrate, siliceous materials such as fumed silica, hydrated silica (precipitated silica) silica aerogels, aluminum silicates, calcium magnesium silicate, clays, molecular sieves, Wollastonite, E-glass, S-glass, A-glass and the like.

The resinous material can be a thermoplastic or thermosetting material, and the use of the term "resinous material" does not exclude the possibility that the material is formed in situ and therefore is derived from a monomeric material while in contact with an inorganic oxide material.

The resin medium with which the coupling agents or adhesion promoters of this invention can be suitably employed includes a large number of resins which are known to be reactive with aminosilanes. Included in the definition of plastic are rubber compounds. Suitable plastics and resins include, by way of example, thermoplastic and thermosetting resins and rubber compounds (including thermoplastic elastomers). The plastics and resins, in conjunction with the inorganic oxide materials treated with the latent coupling agents or latent adhesion promoters of this invention, can be employed, for example, for molding (including extrusion, injection, calendering, casting, compression, lamination, and/or transfer molding), coating (including lacquers, film bonding coatings and paints, inks, dyes, tints), impregnations, aadhesives, caulks, sealants, rubber goods, and cellular products.

For simple illustration purposes, the plastics and resins may be alkyd resins, unsaturated polyesters, natural oils, (e.g., linseed, tung, soybean), epoxies, nylons, thermoplastic polyester (e.g., polyethylene-terephthalate, polybutyleneterephthalate), polycarbonates, polyethylenes, polybutylenes, polystyrenes, styrene/butadiene copolymers, polypropylens, ethylene/propylene copolymers and terpolymers, silicone resins and rubbers, SBR rubbers, nitrile rubbers, natural rubbers, acrylics (homopolymer and copolymers of acrylic acid, acrylates, methacrylates, acrylamides, their salts, hydrohalides, and the like), phenolic resins, polyoxymethylene (homopolymers and copolymers), polyurethanes, polysulfones, polylsulfide rubbers, vinyl butyrates, vinyls (vinyl chloride and/or vinyl acetate containing polymers), viscose rayon, shellac waxes, ethylene copolymers (e.g., ethylene-vinyl acetate copolymers, ethylene-acrylic acid copolymers, ethylene-acrylate coplymers), and the like.

If desired, the latent coupling agents or latent adhesion promoters of this invention can be employed in combination with any of the coupling agents known in the art.

Generally, the latent coupling agent or latent adhesion promoters of this invention serve the function when activated (deblocked) of enhancing bonding between the resinous medium and inorganic oxide surface. The latent coupling agent may render the inorganic oxide surface more compatible with the resinous medium and protect the oxide surface. The former function increases wettability and dispersibility of particulate or fibrous fillers, pigments and the like in the resinous medium and renders the latent coupling agents when activated particularly useful in improving the bonding of coatings and adhesives to inorganic oxide substrates. The latter function prevents abrasion or corrosion to the inorganic oxide substrate which may result in a weaker oxide surface or glass fiber.

The amount of coupling agent used is that amount which alters the surface characteristics of the inorganic oxide surfaces so that they are more compatible with and/or adherent to the resinous medium within which they are incorporated. When the latent coupling agent is supplied to the resin by the integral blending technique, the effective amount of the coupling agent can vary from about 0.1 weight percent to about 10 weight percent and is preferably from 0.5 weight percent to 2.0 weight percent, based on the weight of the resin. When the coupling agent is supplied directly to the surface of the inorganic oxide material in the form of a fibrous or particulate filler, pigment or the like, the effective amount can vary from about 0.01 weight percent to about 10 weight percent, and is preferably from 0.1 weight percent to about 0.5 weight percent based on the weight of the inorganic oxide material. When applying a solution of the latent coupling agent or latent adhesion promoter as a primer to a surface of inorganic oxide, the effective amount of latent coupling agent applied to the surface can vary from about 0.005 grams/m² to about 1.5 grams/m², and is preferably from about 0.01 grams/m² to 0.1 grams/m², calculated as the weight of coupling agent or adhesion promoter (exclusive of solvent) per square meter of inorganic oxide surface treated.

The following examples are illustrative of the invention.

EXAMPLE 1

Synthesis of Tert-butyl N-(3-trimethoxysilylpropyl) carbamate

Into a 50 ml round bottom flask was charged carbon tetrachloride (10.71 gms.) and 3-isocyanatopropyltrimethoxysilane (10.04 gms., 0.049 moles). Over a three minute period, tert-butyl alcohol (3.6 gms., 0.049 moles) was added at 21° C. The mixture was heated at 81° to 84° C. for 4.5 hours. $^1$-H NMR of the reaction mixture indicated the reaction of tert-butyl alcohol with both the isocyanate group and the silicon ester. Vacuum distillation of the mixture at 104° C. at 0.08 mm Hg yields a product that was only 55% pure.

EXAMPLE 2

Synthesis of Tert-butyl N-(3-trimethoxysilylpropyl) carbamate

Into a 100 ml three-necked flask was charged tert-buty N-allyl carbamate (20.0 gms., 0.13 mole) and toluene (18.0 gms.). The mixture was heated to 110° C. and catalyzed with 100 ppm chloroplatinic acid. Trimethoxysilane (15.86 gms, 0.13 mole) was added and heated at 104° C. for 45 minutes. The reaction mixture was allowed to stand overnight. The next day, the reaction was heated to 104°-108° C. and catalyzed twice with the chloroplatinic acid. The reaction was heated for several hours. After allowing the reaction to stand for 3 days, the reaction was nearly complete. The mixture was heated to 112° C. and recatalyzed, and heated for 3 hours. The mixture was vacuum distilled at 112°-119° C. at 1.2 mm to yield essentially pure product.

EXAMPLE 3

Decomposition of Tert-butyl N-(3-trimethoxysilylpropyl) carbamate

Into a 50 ml three-necked flask that was being flushed with nitrogen was charged 20.03 gms of tert-butyl N-(3-trimethoxysilylpropyl) carbamate. The material was heated. At 170° C. gassing was observed and pot temperature decreased to 155° C. The material was heated for 1 hour. The material was heated for an additional 1.5 hours at 131° C. The GC of the material detected the presence of 3-aminopropyltrimethoxysilane. The TGA of the tert-butyl N-(3-trimethoxysilylpropyl) carbamate indicated a loss in weight starting at approximately 105° C. with the maximum loss occuring at 195° C. The DSC showed a negative energy flow starting at 110° C. with the maximum at 240° C. There was also a positive energy flow at higher temperatures, probably due to the distillation of 3-aminopropyltrimethoxysilane.

EXAMPLE 4

Synthesis of Tert-butyl N-(3-trimethoxysilylpropyl) carbamate

Into a 3-neck round bottom flask equipped with a thermometer, dropping funnel and a nitrogen line, was added tert-butyl phenyl carbonate (9.71 gms., 0.050 moles) and dimethyl formamide (10 gms.). 3-Aminopropyltrimethoxysilane (8.61 gms., 0.048 moles) was slowly added at 25° C. with stirring. An exotherm raised the temperature to 32° C. The reaction was stirred at room temperature for 24 hours. A GC showed the formation of a new peak with retention time 16.30 min. (3-aminopropyltrimethoxysilane had a retention time of 12.26 min., phenol had a retention time of 8.01 min., tert-butyl phenyl carbonate had a retention time of 12.84 min. and tert-butyl alcohol had a retention time of 2.44 min.; GC conditions were OV 101 on Chromasorb W-HP ¼"×6', 50° C. initial temperature, program rate of 10° C./minute, final temperature of 295° C.). The reaction mixture stood for an additional 3 days. The dimethyl formamide was removed by rotovap at 5 mm Hg at 50° C. A clear liquid (10.16 gms) was collected. It dissolved in n-hexane (25 gms) and extracted twice wih a 5% sodium carbonate solution that was cooled to 5° C. The organic layer was isolated and dried over magnesium sulfate. The n-hexane was removed on a rotovap to yield 4.47 gms of an oil. 1-H NMR indicated only the presence of phenol and 3-aminopropyltrimethoxysilane confirming that a blocked carbamate silicon compound was formed and decomposed during work-up.

EXAMPLE 5

Synthesis of Tert-butyl N-(3-triethoxysilylpropyl) carbamate

Into a 100 ml three-necked flask were charged di-tert-butyl dicarbonate (24.7 gms, 0.113 mole) and tetrahydrofuran (20.0 gms). The mixture was cooled by a water bath, and gamma-aminopropyltriethoxysilane (24.04 gms, 0.113 mole) was added with a rise in temperature to 32 degrees C. Vacuum distillation provided the desired product, tert-butyl N-(3-triethoxysilylpropyl) carbamate, at 118-120 degrees C. at 0.15 mm Hg, with the structure confirmed by NMR.

EXAMPLE 6

Decomposition of Tert-butyl N-(3-triethoxysilylpropyl) carbamate

Into a 25 ml three-necked flask that was being flushed with nitrogen were charged 7.04 gms of tert-butyl N-(3-triethoxysilylpropyl) carbamate. The material was heated, and at 213 degrees C., gassing was observed and pot temperature decreased to 173 degrees after 30 minutes. The GC of the material detected no gamma-aminopropyltriethoxysilane. The NMR data suggests a urea like structure confirming that 3-aminopropyltriethoxysilane had formed.

EXAMPLE 7

Synthesis of Tert-butyl N-allyl carbamate

The procedure of Example 5 was repeated using di-tert-butyl dicarbonate (40.14 gms, 0.19 mole), allyl amine (10.83 gms, 0.18 mole), and tetrahydrofuran (20.11 gms). The maximum temperature during the addition was 37 degrees C. The mixture was vacuum stripped to produce a white solid which was purified by distillation at 44 degrees C. at 0.32 mm Hg. NMR analysis confirmed the structure.

EXAMPLE 8

Synthesis of Tert-butyl N-(trimethoxysilylpropyl) carbamate

The procedure of Example 5 was repeated using di-tert-butyl dicarbonate (26.68 gms, 0.12 mole), gamma-aminopropyltrimethoxysilane (21.91 gms, 0.12 mole), and tetrahydrofuran (15.0 gms). The maximum temperature during the addition was 35 degrees C. Vacuum distillation produced the desired product, tert-butyl N-(trimethoxysilylpropyl) carbamate, at 107 degrees C. at 0.25 mm Hg., with the structure confirmed by NMR.

EXAMPLE 9

Decomposition of Tert-butyl N-(3-trimethoxysilylpropyl) Carbamate

The procedure of Example 6 was repeated using 6.65 gms tert-butyl N-(3-trimethoxysilylpropyl) carbamate. The material was heated to 205 degrees C. After 3 hours the reflux temperature had dropped to 151 degrees C. Isocyanatopropyltrimethoxysilane was isolated by vacuum distillation, and its structure confirmed by NMR. The non-distilled fraction contained urea groups, confirming formation of aminosilane.

EXAMPLE 10

Synthesis of Tert-butyl N-methyl-N-(3-trimethoxypropyl) carbamate

The procedure of Example 5 was repeated using di-tert-butyl dicarbonate (22.32 gms, 0.10 mole), N-methylaminopropyltrimethoxysilane (19.79 gms, 0.10 mole), and tetrahydrofuran (12:0 gms). The maximum temperature reached during the addition of N-methylaminopropyltrimethoxysilane was 35 degrees C. Tert-butyl N-methyl-N-(3-trimethoxysilylpropyl) carbamate was isolated by distillation at >96 degrees C. at 0.25 mm Hg, and its structure confirmed by NMR.

EXAMPLE 11

Decomposition of Tert-butyl N-methyl-N-(3-trimethoxysilylpropyl) carbamate

The procedure of Example 6 was repeated using 3.99 gms tert-butyl N-(3-trimethoxysilylpropyl) carbamate. The material was heated to 225 degrees C. with a temperature drop of 23 degrees seen after 90 minutes. Vacuum distillation provided N-methylaminopropyltrimethoxysilane, at 39 degrees C. at 0.25 mm Hg, with the structure confirmed by NMR.

EXAMPLE 12

Synthesis of Di-(tert-butyl carbamate) of 3-[N-(2-aminoethyl)] aminopropyltrimethoxysilane The procedure of Example 5 was repeated using di-tert-butyl dicarbonate (44.47 gms, 0.204 mole), aminoethylaminopropyltrimethoxysilane (24.42 gms, 0.11 mole), and tetrahydrofuran (15.0 gms). The maximum temperature during the reaction was 36 degrees C. Vacuum stripping at 30 degrees C. at 0.6 mm Hg removed lights. The product structure was confirmed by NMR analysis.

EXAMPLE 13

Decomposition of Di-(tert-butyl carbamate) of 3-[N-(2-aminoethyl)]aminopropyltrimethoxysilane The procedure of Example 6 was repeated using 15.1 gms di-(tert-butyl carbamate) of N-(2-aminoethyl)-3-aminopropyltrimethoxysilane. The material was heated to 220 degrees C. After 222 minutes the pot temperature had dropped to 158 degrees C. The material was vacuum distilled and yielded aminoethylaminopropyltrimethoxysilane and aminoethylaminopropyldimethoxy-t-butoxysilane. The product structures were confirmed by NMR analysis.

EXAMPLE 14

Stability of Tert-butyl N-(3-trimethoxysilylpropyl) carbamate and film former size Into a 100 ml beaker was charged methanol (3 gms), tert-butyl N-(3-trimethoxysilylpropyl) carbamate (1.1 gms), acetic acid (0.5 gms) and water (1.0 gms). The mixture was stirred for 15 minutes and then added water (44.5 gms). A hazy solution resulted which cleared in approximately 1 minute.

A water borne phenoxy resin (Union Carbide PKHW-35) at 40% solids (15 gms) was mixed with water (35 gms). The solution was then slowly added to the dilute solution of the tert-butyl N-(3-trimethoxysilylpropyl) carbamate hydrolyzate. The resulting mixture was stable.

EXAMPLE 15

Stability of 3-aminopropyltrimethoxysilane and Phenoxy Film Former Size

The same procedure that was described in Example 14 was run except the silane was 3-aminopropyltrimethoxysilane. The mixture of the silane and the PKHW-35 phenoxy resin resulted in precipitation of a white cheesy solid.

EXAMPLE 16

Fiberglass Sized with Tert-butyl N-(3-trimethoxysilylpropyl) Carbamate in Reinforced Epoxy Composites Into a 125 ml beaker was charged methanol (9 gms)( acetic acid (0.5 gms), tert-butyl N-(3-trimethoxysilylpropyl) carbamate (3 gms) and water (1 gm). The mixture was stirred for 20 minutes. While stirring, water (86.5 gms) was added. A very hazy solution resulted. After 1 minute, the solution cleared. The clear solution was added to water (500 gms).

OCF-861 glass fiber was coated with the 0.5% aqueous solution by drawing the glass fiber through the solution at a draw rate of 30 feet per minute. The coated glass was dried by drawing the glass through a heated cylindrical tube that was 12 feet long and 6 inches in diameter. The tube was flushed with air that was heated to 280° C. The dried glass was gathered onto a spool. The coated glass fiber was then wound 22 times around a rectangular metal frame that was 36 inches long. One end of the glass roving was tied with a copper wire. The other end of the roving was cut.

Epon 828 (350 gms) was heated to 70° C. in a quart bottle. Melted phenylenediamine (52.8 gms) was added to the Epon 828 and mixed. The contents of the bottle were poured into an aluminum foil lined stainless steel tray that was 40 inches long, 4 inches wide and 2 inches deep that contained the glass roving. The glass roving was then immediately pulled through a 0.25 inch precision bore glass tube by pulling on the copper wire at a draw rate of 1 foot per minute. The glass tube, resin and glass fiber were placed into a forced air, Despatch oven and cured at 150° C. for 1 hour and then cooled to room temperature. The pultruded glass fiber reinforced epoxy composite was removed from the glass tube and cut into 2.25 inch lengths.

The dry flexural strength was determined by breaking the pultruded composite on an Instron 1123. The diameter of the pultruded composite was precisely measured using an Ames micrometer. The sample was broken on the Instron using a crosshead speed of 0.2 inch per minute with a 1.75 inch span. The dry flexural strength was calculated using the equation:

$$\text{flexural strength} = (8fl)/(\pi d^3)$$

where
 l = length of span
 f = force necessary to break sample
 $\pi$ = pi, 3.14
 d = diameter of sample
The flexural strengths that were reported were the average of six test samples.

The wet flexural strength was determined by boiling the samples in water for 24 hours, and then following the procedure outlined for dry flexural strengths.

The amount of size on the glass was determined by burning off the size (loss on ignition). A small sample of the glass fiber (approximately 7 grams) was carefully weighed on a Mettler Analytical Balance. The glass was placed into a Blue M muffle furnace set at 600° C. for 2 hours, removed and cooled in a desiccator and weighed. The weight percent loss on ignition was calculated using the equation:

$$\text{LOI } \% = [(wI - wF)/wI]100$$

where
 wI = initial weight of glass
 wF = final weight of glass after burning off the coating.

The glass content of the pultruded glass fiber reinforced composite was determined by burning off the organic material of the composite. A 2.25 inch pultruded rod was carefully weighed on a Mettler Analytical Balance. The sample was placed into a Blue M muffles furnace set at 600° C. for 2 hours, removed, cooled in a desiccator and weighed. The glass content of the composite was calculated using the equation:

$$\text{glass content } \% = [(w'I - w'F)/w'I]100$$

where
 w'I = initial weight of the composite
 w'F = weight of the residue after burning.
It was found that:
 dry flexural strength was 107,000 psi
 wet flexural strength was 95,000 psi
 loss on ignition was 0.30%
 glass content of the composite was 62.0%.

EXAMPLE 17

Fiberglass Sized with Tert-butyl N-(3-trimethoxysilylpropyl) Carbamate in Reinforced Composites A composite was made and tested according to the procedure described in Example 16, except that the glass roving was postcured at 170° C. for 2 hours before it was used to make the composite. It was found that:
 dry flexural strength was 120,000 psi
 wet flexural strength was 101,000 psi
 loss on ignition was 0.30%
 glass content of the composite was 60.9%.

EXAMPLE 18

Fiberglass Sized with 3-Aminopropyltriethoxysilane in Reinforced Composites

3-Aminopropyltriethoxysilane (2.0 gms) was added to water (398 gms). The solution was used to size fiberglass, and the resultant glass was used to make composites, as described in Example 16. It was found that:
 dry flexural strength was 86,000 psi
 wet flexural strength was 86,000 psi
 loss on ingnition was 0.18%
 glass content of the composite was 63.1%.

EXAMPLE 19

Abrasion Resistance of Tert-butyl N-(3-trimethoxysilylpropyl) Carbamate Sized Fiberglass The silane sized fiberglass described in Example 16 was tested for abrasion resistance. The resistance of the glass to fiber-fiber abrasion was measured to determine the protection that the size provide to the strand. The abrasion resistance was measured using a custom designed abrasion tester. The tester consisted of a motor gear arrangement that oscillated a metal shaft back and forth through a 90 degree arc. Attached to the shaft was a cylinder that was 5.5 inches in diameter and was grooved to hold the glass strand in place. The tester also consisted of a cylinder that was made out of aluminum that was 5.5 inches and diameter and 3/16 inches in height that also contained a groove. The free standing cylinder weighed 195 grams. The strand of glass was tied into a loop of sufficient length so that when the strand was placed into the grooves of the rotating and free standing cylinders the distance between the centers of the two cylinders was 16 inches. The free standing cylinder was rotated 360 degrees out of the plane of its axis in order to make a loop of glass into a figure "8" arrangement that contained one complete twist. The tester also contained a counter that measured the mumber of oscillations of the cylinders. The motor was turned on. When the glass became weakened by the fiber-fiber abrasion, the 195 gram weight would eventully be sufficient to break the strand. The free standing cylinder would fall and trip a switch that would stop the counting of the oscillations. The time to failure (minutes) was found to be 1.5 minutes.

EXAMPLE 20

Abrasion Resistance of Tert-butyl N-(3-trimethoxysilylpropyl) Carbamate Sized glass The fiberglass prepared in Example 17 was measured for abrasion resistance as described in Example 19. It was found that the time to break was 0.9 minutes confirming that some of the t-butyl carbamate had decomposed to form the free amine.

EXAMPLE 21

Abrasion Resistance of 3-Aminopropyltriethoxysilane Sized glass

The fiberglass prepared in Example 18 was measured for abrasion resistance as described in Example 19. It was found that the time to break was 0.5 minutes.

EXAMPLE 22

Synthesis of Tert-amyl N-(3-trimethoxysilylpropyl) Carbamate

Into a 100 ml three-necked flask were charged isocyanatopropyltrimethoxysilane (20.0 gms, 0.1 mole), tert-amyl alcohol (8.80 gms, 0.1 mole), and tetrahydrofuran (10.0 gms). The mixture was heated to 93 degrees C. Triethylamine was added to initiate product formation. Vacuum distillation produced the desired product, tert-amyl N-(trimethoxysilylpropyl) carbamate, at 115 degrees C. and 1 mm Hg., with the structure confirmed by NMR.

EXAMPLE 23

Decomposition of Tert-amyl N-(3-trimethoxysilylpropyl) Carbamate

The procedure of Example 6 was repeated using 5.0 gms t-amyl N-(3-trimethoxysilylpropyl) carbamate. The material was heated to 201 degrees C. After six hours GC analysis detected decomposition products, consisting of methyl N-(3-trimethoxysilylpropyl) carbamate and a urea like structure.

EXAMPLE 24

Synthesis of Tert-butyl N,N-bis(trimethoxysilylpropyl) Carbamate

The procedure of Example 5 was repeated using di-tert-butyl dicarbonate (8.22 gms, 0.038 mole), bis-(3-trimethoxysilylpropyl) amine (12.86 gms, 0.038 mole), and tetrahydrofuran (8.0 gms). The maximum temperature during additon was 27 degrees C. Tert-butyl N,N-bi(trimethoxysilylpropyl) carbamate was isolated by vacuum distillation at 145 degrees C. and 0.15 mm Hg, and its structure confirmed by NMR.

EXAMPLE 25

Decomposition of Tert-butyl N,N-bis(trimethoxysilylpropyl) Carbamate

The procedure of Example 6 was repeated using 8.03 gms of tert-butyl N,N-bis(trimethoxysilylpropyl) carbamate. The material was heated for four hours with a maximum temperature of 250 degrees C. Bis-(3-trimethoxysilylpropyl)amine was isolated by vacuum distillation at 112 degrees C. and 0.08 mm Hg. The structure was confirmed by NMR analysis.

EXAMPLE 26

Synthesis of 2-[2-methyl-3-butenyl] N-allyl Carbamate

The procedure of Example 1 was repeated using 2-methyl-3-buten-2-ol (10.95 gms, 0.13 mole) and allyl isocyanate (10.00 gms, 0.12 mole). The maximum temperature during the addition was 28 degrees C. Vacuum distillation provided 2-[2-methyl-3-butenyl] N-allyl carbamate, at 59 degrees and 0.5 mm Hg, with the structure confirmed by NMR.

EXAMPLE 27

Synthesis of 2-[2-methyl-3-butenyl] N-(3-trimethoxysilylpropyl) Carbamate

Into a 50 ml three-neck flask were charged 2-[2-methyl-3-butenyl] N-allyl carbamate (8.0 gms, 0.047 mole) and toluene (5.0 gms). Trimethoxysilane (5.73 gms, 0.047 mole) was charged into an addition funnel. The mixture was heated to 105 degrees C. and 0.0035 ml chloroplatinic acid solution (corresponding to 50 parts per million platinum) was added while stirring rapidly under nitrogen. Trimethoxysilane was then added dropwise with a gradual drop in temperature to 94 degrees C. The temperature was then maintained at 104 degrees C. Analysis by gas chromatography (GC) showed unreacted 2-[2-methyl-3-butenyl] N-allyl carbamate. An additional 0.0035 ml catalyst and 2.10 gms trimethoxysilane were added to convert the unreacted olefin. Vacuum distillation provided the desired product, at 95 degrees C. and 0.07 mm Hg, with the structure confirmed by NMR.

EXAMPLE 28

Decomposition of 2-(2-Methyl-3-butenyl) N-(3-trimethoxysilylpropyl) Carbamate Into a 25 ml flask fitted with a vacuum take off adapter was charged 2-(2-methyl-3-butenyl) N-(3-trimethoxysilylpropyl) carbamate (4.87 gms, 0.017 mole). The atmospheric pressure was reduced to 0.6 mm Hg and the mixture was heated. At 170 degrees C. gassing was observed, and the mixture was heated for an additional 16 minutes with a maximum temperature of 195 degrees C. The decomposition products of isoprene, 2-methyl-3-buten-2-ol, and methanol were confirmed by NMR analysis.

Although the invention has been illustrated by the preceding examples, it is not to be construed as being limited to the materials employed therein, but rather, the invention is directed to the generic area as hereinbefore disclosed. Various modifications and embodiments thereof can be made without departing from the spirit or scope thereof.

What is claimed is:

1. A tert-alkyl carbamate silicon compound having the following unit structure:

(I)

wherein $R^3$ contains 1 to 10 carbon atoms and represent a saturated or unsaturated aliphatic group or an aryl group with the proviso that the $R^3$ groups need not be the same and contain at least one alkyl group having an alpha-carbon with at least one hydrogen, and wherein the remainder of the molecule contains at least one silicon atom and from 1 to 90 carbon atoms, wherein the unit structure is attached to the silicon atom through a carbon linkage, and wherein the tert-alkyl carbamate silicon compound can also contain one or more of nitrogen, oxygen or halogen.

2. A tert-alkyl carbamate silicon compound selected from the group consisting of

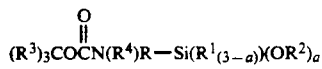
(II)

and

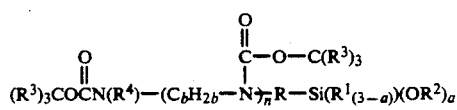
(III)

wherein:

R contains 1 to 20 carbon atoms and represents an arylene group, an alkarylene group or a branched or straight chain, unsaturated or saturated group of the structure:

(V)

wherein x, y, and z have a value of from 0 to 20 and wherein the sum of x, y, and z is at least 1, but not greater than 20 and wherein $R^5$ is an alkyl group of 1 to 6 carbon atoms, $R^1$ contains 1 to 10 carbon atoms, and represents a straight or branched chain alkyl group, an aryl group, or an alkaryl group;

$R^2$ is the same as $R^1$ and may additionally represent hydrogen, acyl, alkoxyalkyl, $CH_3OCH_2CH_2-$, $CH_3OCH(CH_3)CH_2-$, $N=C(R')(R'')$ wherein $R'$ and $R''$ are lower alkyl, and silyl groups including the hydrolytic conensation products thereof;

$R^3$ contains 1 to 10 carbon atoms, and represents a saturated or unsaturated aliphatic group or an aryl group with the proviso that the $R^3$ groups need not be the same and the formula (I) must contain at least one $R^3$ alkyl group and which contains an alpha-carbon with at least one hydrogen;

$R^4$ represents hydrogen, aryl, or a straight or branched chain alkyl group of 1 to 10 carbon atoms, or

wherein R, $R^1$ and $R^2$ are as previously indicated; n has a value of 1 to 10, b has a value of 2 to 5 and a has a value of 1,2 or 3.

3. A tert-alkyl carbamate silicon compound of the formula:

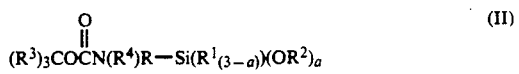
(II)

wherein:

R-$R^4$, and a are as indicated in claim 2.

4. A tert-alkyl carbamate silicon compound of the formula:

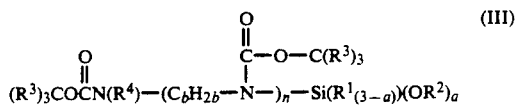
(III)

wherein:

R-$R^4$, n and a are as indicated in claim 2.

5. The compound of claim 2 wherein R is alkylene, $R^1$-$R^3$ are alkyl, $R^4$ is hydrogen and a is 3.

6. The compound of claim 2 wherein R is alkylene, $R^1$-$R^3$ are alkyl, $R^4$ is hydrogen and a is 2.

7. The compound of claim 2 wherein R is alkylene, $R^1$-$R^3$ are alkyl, $R^4$ is hydrogen and a is 1.

8. The compound of claim 2 wherein R is alkylene and contains at least 3 carbon atoms.

9. The compound of claim 2 wherein at least one $R^3$ group contains an alpha-carbon atom with at least one hydrogen.

10. The compound of claim 2 wherein $R^2$ and $R^3$ are lower alkyl and a is 3.

11. The compound of claim 2 which is tert-butyl N-(3-trimethoxysilylpropyl) carbamate.

12. The compound of claim 2 which is tert-butyl N-(3-triethoxysilylpropyl) carbamate.

13. The compound of claim 2 which is tert-butyl N-methyl-N-(3-trimethoxysilylpropyl) carbamate.

14. The compound of claim 2 which is di-(tert-butyl carbamate) of 3-[N-(2-aminoethyl)]aminopropyltrimethoxysilane 15. The compound of claim 2 which is tert-amyl-N-(trimethoxysilylpropyl) carbamate.

16. The compound of claim 2 which is tert-butyl N,N-bis(trimethoxysilylpropyl) carbamate.

17. The compound of claim 2 which is 2-(2-methyl-3-butenyl) N-(3-trimethoxysilylpropyl) carbamate.

18. A process for preparing a compound of the formula:

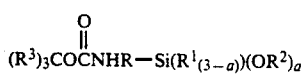

wherein:
R contains 1 to 20 carbon atoms and represents an arylene group, an alkarylene group or a branched or straight chain, unsaturated or saturated group of the structure:

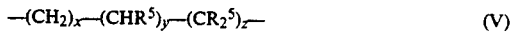 (V)

wherein x, y, and z have a value of from 0 to 20 and wherein the sum of x, y, and z is at least 1, but not greater than 20 and wherein $R^5$ is an alkyl group of 1 to 6 carbon atoms, $R^1$ contains 1 to 10 carbon atoms, and represents a straight or branched chain alkyl group, an aryl group, or an alkaryl group;

$R^2$ is the same as $R^1$ and may additionally represent hydrogen, acyl, alkoxyalkyl, $CH_3OCH_2CH_2$—, $CH_3OCH(CH_3)CH_2$—, $N=C(R')(R'')$ wherein $R'$ and $R''$ are lower alkyl, and silyl groups including the hydrolytic conensation products thereof;

$R^3$ contains 1 to 10 carbon atoms, and represents a saturated or unsaturated aliphatic group or an aryl group with the proviso that the $R^3$ groups need not be the same and the formula (I) must contain at least one alkyl group $R^3$ which contains an alpha-carbon with at least one hydrogen; wherein a has a value of 1, 2 or 3, which comprises reacting a compound of the formula:

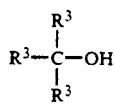

with a compound of the formula:

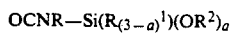

wherein R-$R^3$ are as indicated and thereafter recovering said carbamate.

19. The process of claim 18 wherein R is alkylene, $R^1$-$R^3$ are alkyl and a is 3.

20. The process of claim 18 wherein R is alkylene, $R^1$-$R^3$ are alkyl and a is 2.

21. The process of claim 18 wherein R is alkylene, $R^1$-$R^3$ are alkyl and a is 1.

22. The process of claim 18 wherein R is alkylene and contains at least 3 carbon atoms.

23. The process of claim 18 wherein at least one $R^3$ group contains an alpha-carbon atom with at least one hydrogen.

24. The process of claim 18 wherein $R^2$ and $R^3$ are lower alkyl and a is 3.

25. The process of claim 18 which is tert-butyl N-(3-trimethoxysilylpropyl) carbamate.

26. A process for preparing a compound selected from the group consisting of:

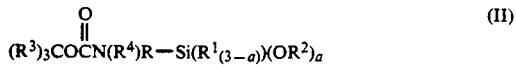 (II)

and

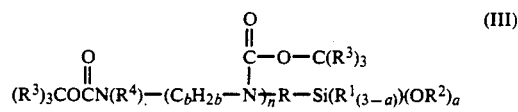 (III)

wherein:
R contains 1 to 20 carbon atoms and represents an arylene group, an alkarylene group or a branched or straight chain, unsaturated or saturated group of the structure:

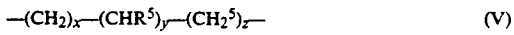 (V)

wherein x, y, and z have a value of from 0 to 20 and wherein the sum of x, y, and z is at least 1, but not greater than 20 and wherein $R^5$ is an alkyl group of 1 to 6 carbon atoms, $R^1$ contains 1 to 10 carbon atoms, and represents a straight or branched chain alkyl group, an aryl group, or an alkaryl group;

$R^2$ is the same as $R^1$ and may additionally represent hydrogen, acyl, alkoxyalkyl, $CH_3OCH_2CH_2$—, $CH_3OCH(CH_3)CH_2$—, $N=C(R')(R'')$ wherein $R'$ and $R''$ are lower alkyl, and silyl groups including the hydrolytic condensation products thereof;

$R^3$ contains 1 to 10 carbon atoms, and represents a saturated or unsaturated aliphatic or aryl group with the proviso that the $R^3$ groups need not be the same and the formula (I) must contain at least one alkyl group $R^3$ which contains an alpha-carbon with at least one hydrogen;

$R^4$ represents hydrogen, aryl, or a straight or branched chain alkyl group of 1 to 10 carbon atoms, or

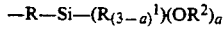

wherein R, $R^1$ and $R^2$ are as previously indicated n has a value of from 1 to 10, b has a value of 2 to 5 and a has a value of 1, 2 or 3;

which comprises reacting a compound selected from the group consisting of:

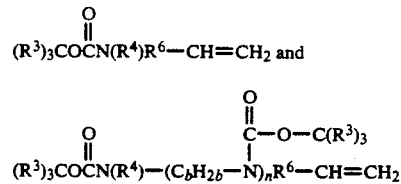

with a compound of the formula:

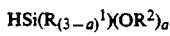

wherein $R^1$-$R^4$ are as indicated, and $R^6$ contains 1 to 18 carbon atoms and represents an arylene group, and alkenylene group or a branched or straight chain unsaturated or saturated group and thereafter recovering said carbamate.

27. The process of claim 26 wherein R is alkylene, $R^1$-$R^3$ are alkyl, $R^4$ is hydrogen and a is 3.

28. The process of claim 26 wherein R is alkylene, $R^1$-$R^3$ are alkyl, $R^4$ is hydrogen and a is 2.

29. The process of claim 26 wherein R is alkylene, $R^1$-$R^3$ are alkyl, $R^4$ is hydrogen and a is 1.

30. The process of claim 26 wherein R is alkylene and contains at least 3 carbon atoms.

31. The process of claim 26 wherein at least one $R^3$ group contains an alpha-carbon atom with at least one hydrogen.

32. The process of claim 26 wherein $R^2$ and $R^3$ are lower alkyl and a is 3.

33. The process of claim 26 which is tert-butyl N-(3-trimethoxysilylpropyl) carbamate.

34. A process for preparing a carbamate compound selected from the group consisting of:

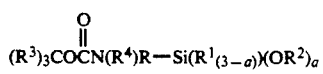

and

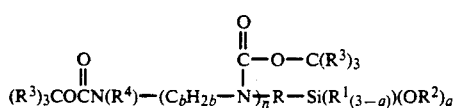

wherein:
R contains 1 to 20 carbon atoms and represents an arylene group, an alkarylene group or a branched or straight chain, unsaturated or saturated group of the structure:

$$-(CH_2)_x-(CHR^5)_y-(CH_2^5)_z- \qquad (V)$$

wherein x, y, and z have a value of from 0 to 20 and wherein the sum of x, y, and z is at least 1, but not greater than 20 and wherein $R^5$ is an alkyl group of 1 to 6 carbon atoms, $R^1$ contains 1 to 10 carbon atoms, and represents a straight or branched chain alkyl group, an aryl group, or an alkaryl group;

$R^2$ is the same as $R^1$ and may additionally represent hydrogen, acyl, alkoxyalkyl, $CH_3OCH_2CH_2-$, $CH_3OCH(CH_3)CH_2-$, $N=C(R')(R'')$ wherein R' and R'' are lower alkyl, and silyl groups including the hydrolytic conensation products thereof;

$R^3$ contains 1 to 10 carbon atoms, and represents a saturated or unsaturated aliphatic or aryl group with the proviso that the $R^3$ groups need not be the same and the formula (I) must contain at least one alkyl group $R^3$ which contains an alpha-carbon with at least one hydrogen;

$R^4$ represents hydrogen, aryl, or a straight or branched chain alkyl group of 1 to 10 carbon atoms, or

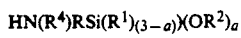

wherein R, $R^1$ and $R^2$ are as previously indicated n has a value of from 1 to 10, b has a value of from 2 to 5 and a has a value of 1, 2 or 3. which comprises reacting a compound selected from the group consisting of:

$$HN(R^4)RSi(R^1)_{(3-a)}(OR^2)_a$$
and
$$HN(R^4)(C_bH_{2b}NH)RSi(R^1)_{(3-a)}(OR^2)_a$$

with a compound of the formula:

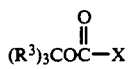

wherein x, n, a, R-$R^4$ are as indicated and X represents Cl, Br, I, or the groups $-O-C_6H_5$, $-OC(R^3)_3$, or

and thereafter recovering said carbamate.

35. The process of claim 34 wherein R is alkylene, $R^1$-$R^3$ are alkyl, $R^4$ is hydrogen and a is 3.

36. The process of claim 34 wherein R is alkylene, $R^1$-$R^3$ are alkyl, $R^4$ is hydrogen and a is 2.

37. The process of claim 34 wherein R is alkylene, $R^1$-$R^3$ are alkyl, $R^4$ is hydrogen and a is 1.

38. The process of claim 34 wherein R is alkylene and contains at least 3 carbon atoms.

39. The process of claim 34 wherein x represents

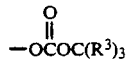

and $R^3$ is methyl.

40. The process of claim 34 wherein at least one $R^3$ group contains an alpha-carbon atom with at least one hydrogen.

41. The process of claim 34 wherein $R^2$ and $R^3$ are lower alkyl and a is 3.

* * * * *